(12) United States Patent
Brooks et al.

(10) Patent No.: US 9,603,623 B2
(45) Date of Patent: Mar. 28, 2017

(54) SYSTEM AND METHOD FOR PERCUTANEOUS SPINE FUSION

(71) Applicant: Wisconsin Alumni Research Foundation, Madison, WI (US)

(72) Inventors: Nathaniel P. Brooks, Madison, WI (US); Meghan A. Anderson, Madison, WI (US); Hannah O. Meyer, Madison, WI (US); Hannah Pezzi, New Berlin, WI (US); Andrea Schuster, Madison, WI (US); Amy R. Slawson, Mequon, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 65 days.

(21) Appl. No.: 14/455,351

(22) Filed: Aug. 8, 2014

(65) Prior Publication Data

US 2016/0038132 A1    Feb. 11, 2016

(51) Int. Cl.
*A61B 17/70* (2006.01)
*A61B 17/34* (2006.01)
(Continued)

(52) U.S. Cl.
CPC ...... *A61B 17/3468* (2013.01); *A61B 17/0293* (2013.01); *A61B 17/7074* (2013.01); *A61B 17/7083* (2013.01); *A61B 17/7097* (2013.01); *A61B 17/88* (2013.01); *A61B 17/8816* (2013.01); *A61F 2/4601* (2013.01); *A61B 2017/0256* (2013.01)

(58) Field of Classification Search
CPC A61B 17/7097; A61B 17/8833; A61F 2/4601

USPC .................................................. 606/86 A
See application file for complete search history.

(56) References Cited

U.S. PATENT DOCUMENTS 6,500,170 B2    12/2002  Palmer et al.
8,945,137 B1 *   2/2015  Greenhalgh ..... A61B 17/00234
                                                     606/93
(Continued)

FOREIGN PATENT DOCUMENTS

WO    2013163226 A1    10/2013

OTHER PUBLICATIONS

Agrawal, et al., Fabrication and Characterization of PLA-PGA Orthopedic Implants, Tissue Engineering, 1995, 1(3):241-252.
(Continued)

*Primary Examiner* — Nicholas Plionis
(74) *Attorney, Agent, or Firm* — Quarles & Brady, LLP (57) ABSTRACT

The present disclosure provides a retractor including an enclosure extending from a first open end to a second open end to form a lumen extending along an axis therebetween and that is accessible from the first open end and the second open end. The retractor further includes a first aperture formed at first angular position in the enclosure, and a second aperture formed at second angular position in the enclosure and opposing the first aperture to form a passage extending transverse to the axis from the first aperture, through the lumen, and to the second aperture. The first aperture and the second aperture are located proximate to the first open end and sized to arrange the passage along a spine of a patient to receive a trocar for delivering a graft material to the spine.

14 Claims, 8 Drawing Sheets

(51) Int. Cl.
  *A61F 2/46* (2006.01)
  *A61B 17/88* (2006.01)
  *A61B 17/02* (2006.01)

(56) References Cited

U.S. PATENT DOCUMENTS

2012/0265019 A1  10/2012  Garcia-Bengochea
2014/0025121 A1   1/2014  Foley et al.
2015/0112352 A1*  4/2015  Krause .................. A61F 2/4601
                                                  606/94

OTHER PUBLICATIONS

Greenstein, et al., The Role of Bone Decortication in Enhancing the Results of Guided Bone Regeneration: A Literature Review, J. Periodontol, 2009, 80:175-189.
Makadia, et al., Poly Lactic-co-Glycolic Acid (PLGA) as Biodegradable Controlled Drug Delivery Carrier, Polymers, 2011, 3:1377-1397.
Roberts, et al., Bone Grafts, Bone Substitutes and Orthobiologics, Organogenesis, 2012, 8(4):114-124.
Williams, et al., Potential of Polyetheretherketone (PEEK) and Carbon-Fibre-Reinforced PEEK in Medical Applications, Journal of Materials Science Letters, 1987, 6:188-190.
Zhang, et al., Experimental Model for Civilian Ballistic Brain Injury Biomechanics Quantification, Journal of Biomechanics, 2007, 40:2341-2346.
Mayo Clinic, Spinal Fusion, www.mayoclinic.com/health/spinal-fusion/MY01235, Copyright 1998-2013 Mayo Foundation for Medical Education and Research.
Mayo Clinic, Spinal Fusion—Results, www.mayoclinic.com/health/spinal-fusion/MY01235/DSECTION=results, Oct. 25, 2012.
Medlineplus, Back Pain, www.nlm.nih.gov/medlineplus/backpain.html, Last Updated: Oct. 18, 2013.
Edwin Haronian, M.D., Spinal Fusion, www.espinedoctor.com/patient-education/procedures/lumbar-procedures/spinal-fusion, Copyright 2012 Espinedoctor.
Green, et al., Back Pain Health Center, Spine, www.webmd.com/back-pain/spine, Last Revised: Feb. 3, 2010.
Frey, Laminectomy Health Article, http://health.yahoo.net/galecontent/laminectomy-1/2, Copyright 2012 Yahoo! Inc.
Medtronic, Minimally Invasive Spinal Surgery, www.medtronic.com/for-healthcare-professionals/products-therapies/spinal/therapies/minimally-invasive-spinal-surgery/index.htm, Last Updated: Sep. 22, 2010.
Medtronic, Infuse Bone Graft/LT-Cage Lumbar Tapered Fusion Device, www.medtronic.com/for-healthcare-professionals/products-therapies/spinal/bone-graft-options/infuse-bone-graft//index.htm, Last Updated: Sep. 22, 2010.
3D Biotek, Medical Devices & Implant Prototypes for Translational Medicine in Tissue Engineering, www.3dbiotek.com/newsletters/2012/Newsletter201211_1_Web.html, Nov. 2012.
Paramount Chiropractic Group, www.paramountchiro.org, 2013.
Depuysynthes, Minimally Invasive Surgery (MIS), Product Family: Viper MIS Spine System, www.depuy.com/healthcare-professionals/product-details/viper-mis-spine-system, Last Updated: Mar. 28, 2013.
Orthofix, Spine—NGage Surgical Mesh System, www.orthofix.com/products/ngage.asp, Copyright 2010 Orthofix Holdings Inc.
Simonovsky, Biomaterials Tutorial—Poly(lactic acid) (PLA) and Poly(glycolic acid) (PGA), www.uweb.engr.washington.edu/research/tutorials/plagla.html, Copyright 2004 University of Washington Engineered Biomaterials.
Sigma-Aldrich Materials Science, Resomer Biodegradable Polymers for Medical Device Applications Research, www.sigmaaldrich.com/materials-science/polymer-science/resomer.html, Copyright 2013 Sigma-Aldrich Co. LLC.
Spineology, Anatomy Conserving Surgery, OptiMesh Product Labeling, www.spineology.com/fb/us/products_us/optimesh.html, Copyright 2009-2016 Spineology.
Ethicon, Vicryla (polyglactin 910) Woven Mesh Product Information, www.ethicon.com/healthcare-professionals/products/hernia-repair-and-fixation, Copyright Ethicon US LLC 2010-2015.
Shapeways, 3D Printing in Stainless Steel on Shapeways, www.shapeways.com/materials/steel, Copyright 2013 Shapeways, Inc.
Mar. 20, 2006 Lumbar Fusion Surgery, www.medicalexhibits.com/obrasky/2007/07049_03XC.jpg.

* cited by examiner

SYSTEM AND METHOD FOR PERCUTANEOUS SPINE FUSION

CROSS-REFERENCE TO RELATED APPLICATIONS

N/A

STATEMENT REGARDING FEDERALLY SPONSORED RESEARCH

N/A

BACKGROUND OF THE INVENTION

The present disclosure relates to systems and methods for delivering a graft material to a spine of a patient with reduced invasiveness. More particularly, the invention relates to a system and method including and utilizing a retractor and trocar configured for positioning a graft material along the spine of a patient with reduced invasiveness.

It is estimated that 8 out of 10 people will be affected by a spine condition during their lifetime, making potential treatment options like spinal fusion surgery an imperative area of surgical improvement. Spinal fusion is a surgical procedure focused on the fusion of two or more vertebrae along the spinal column for the purposes of immobilizing the vertebrae. Spinal fusion procedures can reduce back pain or facilitate the treatment of injuries including broken vertebrae, spinal deformities, spinal weakness, herniated back pain and chronic lower back pain.

In general, a spinal fusion procedure can include joining of two or more vertebrae together using surgical hardware and bone graft material. A typical surgery may include the insertion of both temporary stabilizing hardware and bone graft material. The stabilizing hardware can serve as a temporary solution for spinal stabilization. Specialized screws with heads having compressible clamps can be drilled into the pedicle on the dorsal side of the spine. A metal rod can then be threaded through the screw heads to connect all of the affected vertebrae. Due to the lack of biological integration with the bone, the hardware (e.g., screws, rods) can loosen over time, leading to mechanical failure. Therefore, a bone graft material can be positioned for the fusion of adjacent vertebrae to augment the hardware and contribute to maintaining long-term stability between the affected vertebrae within the spine. Bone graft can be placed in an anterior location between the vertebral bodies or a posterior location across bony elements (e.g. transverse process or lamina).

In the anterior interbody fusion method a graft is typically placed in between the vertebrae. The intervertebral discs are removed prior to decortication. However, this disc removal process can require a relatively lengthy (e.g., less than about 2 hour) surgery. Moreover the surgery can be highly invasive and risks causing injury to the nerves and or spinal fluid leak. The posterior fusion techniques are an alternative procedure which are comparatively less invasive can include the placement of bone graft on the decorticated posterior vertebrae surface lateral to the already implanted stability hardware. Spinal fusion may be induced on either the lamina or transverse processes. However lateral fusion procedures can still be relatively invasive in that a large incision and retraction of the skin and muscles can be required in order to place the bone graft. However, the depth to which the surgeon must cut is less than for intervertebral fusion.

In general, it can be useful to reduce both the length of time a surgery takes as well as the invasiveness of the procedure. So called "minimally invasive" techniques, which seek to perform the underlying procedure with a reduced amount of invasiveness when compared with traditional techniques, can put less stress on the body, minimize scarring, shorten hospital stays, lower healthcare costs, and greatly reduces pain. Statistics have shown that hospital stays are reduced by 60 percent or more as compared with conventional surgery. In addition, recovery from minimally invasive surgery can be faster with less discomfort experienced by the patient. Some of the benefits of minimally invasive procedures may be attributed to decreased blood loss, a lesser potential for injury to surrounding tissue, and a lower chance of infection since there is less exposure of tissue to the outside environment. Overall, a minimally invasive method for providing a posterior bone graft is unknown.

Currently, there exist minimally invasive methods for inserting the stabilizing hardware for spinal fusion percutaneously. The hardware is inserted by providing several small incisions through which to drill the screws into the affected vertebrae. An additional incision allows for the insertion and guidance of the metal rod. However, as the existing stability framework of screws and rods can begin to loosen over time (e.g., within about six to eight weeks), there remains a need to provide a graft material for long-term stability of the spine. Accordingly, there is a need for a system and methods for the implantation of bone graft material in a minimally invasive manner.

SUMMARY OF THE INVENTION

The present disclosure overcomes the aforementioned drawbacks by providing a retractor including an enclosure extending from a first open end to a second open end to form a lumen extending along an axis therebetween and that is accessible from the first open end and the second open end. The retractor further includes a first aperture formed at first angular position in the enclosure, and a second aperture formed at second angular position in the enclosure and opposing the first aperture to form a passage extending transverse to the axis from the first aperture, through the lumen, and to the second aperture. The first aperture and the second aperture are located proximate to the first open end and sized to arrange the passage along a spine of a patient to receive a trocar for delivering a graft material to the spine.

In another aspect, the present disclosure provides a method for delivering a graft material to a spine of a patient. The method includes inserting at least one retractor forming an enclosure extending between a first open end to a second open end and having a passage located proximate to the first open end that extends through the enclosure to arrange the passage along the spine of the patient. The method further includes guiding a trocar along the spine of the patient and through the passage of at least one retractor. The trocar includes an elongate rod having a first open end and defining an interior space for receiving the graft material. The method further includes viewing the trocar through at least one retractor to arrange the trocar along the spine of the patient, disengaging the graft material from the trocar, and removing the trocar from the passage of the at least one retractor, thereby delivering the graft material to the spine of the patient.

In a further aspect, the present disclosure provides a kit for delivering graft material to a spine of a patient, including at least one retractor for insertion in an incision proximal to a spine of a patient. The retractor includes an enclosure extending from a first open end to a second open end, a first aperture formed in the enclosure at first angular position in the enclosure, and a second aperture formed in the enclosure at second angular position in the enclosure and opposing the first aperture. The kit further includes a trocar for delivering a graft material to the spine of the patient through the first aperture and the second aperture of the at least one retractor. The trocar includes an elongated rod having a first open end and defining an interior space for receiving the graft material.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 21A-21D are a top plan view showing still another configuration of the assembly of FIG. 18 positioned along the spine of a patient.

DETAILED DESCRIPTION OF THE INVENTION

The present disclosure provides systems and methods for the implantation of bone graft material. The systems may facilitate and the methods may include one or more minimally invasive techniques for treating the spine of a patient. In one aspect, the present systems and methods may include or be compatible with one or more minimally invasive procedures such as the drilling and decorticating of damaged vertebrae, the insertion and attachment of short-term stability hardware, or the passing of bone graft material lateral to the hardware. Moreover, the present disclosure can include a method in which a user, such as a surgeon, may visually confirm the device positioning as it is guided through the patient. Accordingly, the system and method can achieve long-term spinal stability such as in the case of trauma patients.

In some arrangement, the present systems may facilitate and methods may include one or more minimally invasive techniques for effecting spinal fusion in a patient. A spinal fusion method according to the present disclosure may be carried out to control movement from occurring between the fused vertebrae, increase overall stability, or alleviate pain. A typical spinal injury may call for fusion of anywhere from two or more vertebrae. In some embodiments, the system and method may be applicable to treating conditions such as spondylolisthesis, abnormal curvature seen with scoliosis and kyphosis, a weakened or unstable spine caused by infection and tumor, injury and fracture to the bones, trauma cases, and degenerative diseases.

The fusion process may rely on the natural regenerative nature of bone tissue, in which progenitor cells known as osteoblasts regulate the dynamic process of bone formation. Osteoblasts from the bone graft may form new bone between the graft and the vertebrae, effectively fusing them together. Fusion may not be sufficient for full spinal support until about six to eight weeks after implantation of the graft, which may necessitate a temporary solution for stabilizing the spine. Full fusion of the spine may require three or more months.

To prepare the bone for spinal fusion, a surgeon or other skilled practitioner may first decorticate the surface of the transverse processes. Through the use of tubular retractors, the surgeon may access the bone surface with a decorticating drill and remove the outer cortex layer of the bone until the point that the vertebrae are expelling blood. In one aspect, the blood supply may provide the bone graft with blood and growth factors for fostering osteoinduction and osteoconduction. Decortication may also allow osteoblasts access to the cancellous bone or enhance the physical connection between a bone graft and the spine aiding their fusion.

In one example of a system and method, a trocar may be used to deliver a graft material to the decorticated transverse processes of a patient's spine. One or more retractors as described herein may be inserted proximate the vertebrae of the patient. The first end of the trocar may be passed through an initial incision and inserted into the tissue by the user. The trocar may then be guided along the decorticated transverse processes of the patient's spine. In one aspect, the trocar may be guided through features in the one or more retractors. In another aspect, the one or more retractors may provide a visual confirmation of the location of the trocar within the patient. Upon the alignment of the bone graft along the target vertebra, the bone graft may be delivered and secured in place, such as with a biodegradable suture.

Retractors placed on each vertebra may provide the user with a visual down to the bone graft. Moreover, the retractors may enable the user to grasp the end of the bone graft, securing it in place along the spine. Securing the graft material by hand, with a suture or by another means may reduce the potential for shifting of the graft material to occur during retraction of the trocar from the patient. The trocar may then be retracted through the original incision used for insertion.

In some embodiments, the present system and method may include one or more retractors configured for delivering a graft material to the spine of a patient. Retractors are devices that may be relied upon by a surgeon to displace tissues such as muscle and skin to provide access to underlying tissues, organs, bones and the like. In one example, a retractor may be used to separate the edges of a surgical incision or wound. In another example, a retractor may be used to displace or hold back organs or other tissues. In general, minimally invasive techniques for spinal fusion surgery may include retractors configured for inserting pedicle screws or other like hardware to into a patient's spine. Such retractors may have a basic, cylindrical construction. However, as will be described, such retractors are not configured for use in or sufficiently able to facilitate the methods of the present disclosure that substantially reduce the invasiveness of the process, even when compared with traditional notions of so-called "minimally-invasive" procedures.

With reference to FIGS. 1-4, an embodiments of a retractor 10 can include a body or enclosure 12 extending from a first open end 14 (proximal end) to a second open end 16 (distal end) to form a lumen 18 extending along a longitudinal axis, A, that extends between the first open 14 end and the second open end 16. The lumen 18 may be accessible from the first open end 14 and the second open end 16. In one aspect, the enclosure 12 proximate the first open end 14 is sized to be receivable within an incision in a patient to engage a spine of the patient. In one aspect, the body or enclosure 12 may be formed as a single component without movable or ancillary attached components to thereby provide a desirable body or enclosure 12 that is fixed and/or continuous in design. In another aspect, the enclosure 12 may define a generally cylindrical body. However, the overall size, shape and dimensions of the retractor 10 may be varied without departing from the scope of the present disclosure. To this end, the lumen 18 may take the shape of an oval, irregular shape, triangle, rectangle, hexagon, and the like.

Figures 1, 2:
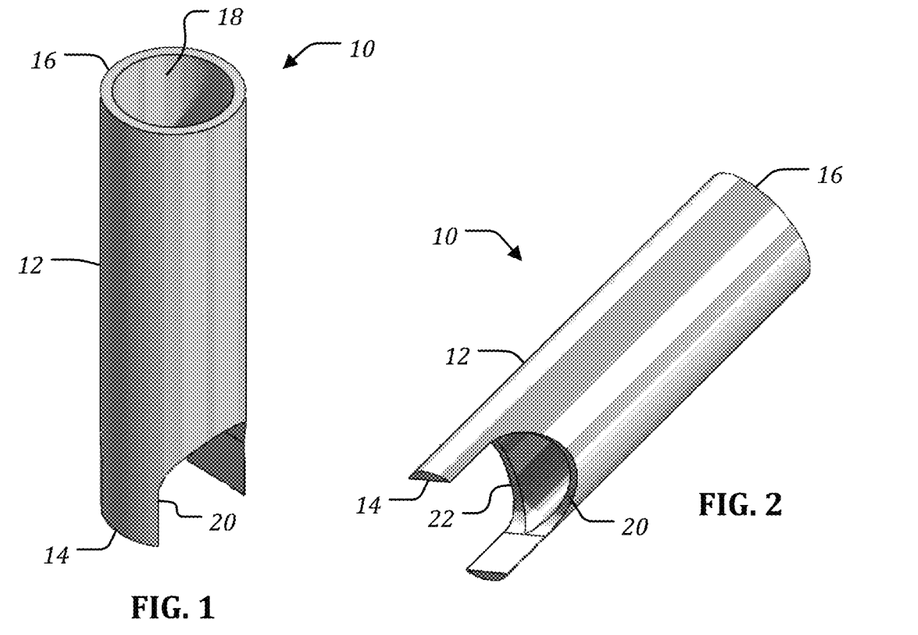
FIG. 1 is a perspective view of an example retractor according to the present disclosure.
FIG. 2 is an alternate perspective view of the retractor of FIG. 1.
Figure 3:
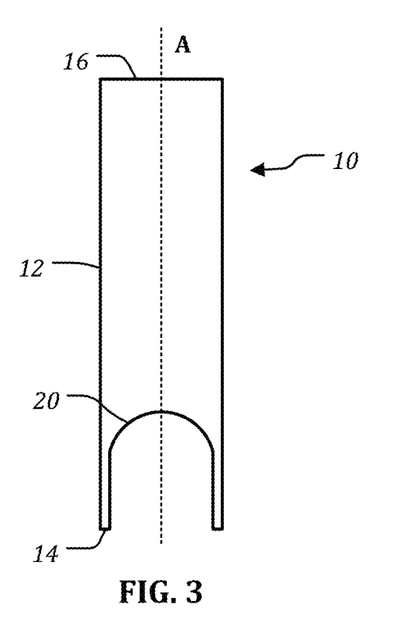
FIG. 3 is a front elevational view of the retractor of FIG. 1.
Figure 4:
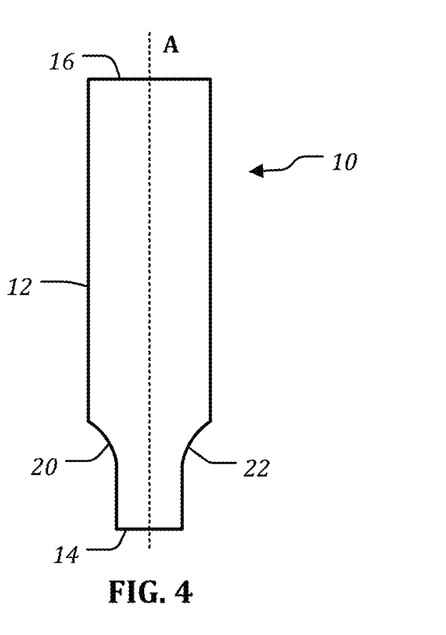
FIG. 4 is a side elevational view of the retractor of the retractor of FIG. 3.

The retractor 10 can further include a first aperture 20 and a second aperture 22 formed in the enclosure 12. The first aperture 20 and the second aperture 22 may be located proximate the first open end 14. For example, the first aperture 20 and the second aperture 22 may extend in a longitudinal direction along the length of the enclosure 12 from the first open end 14. In one aspect, the first aperture 20 and second aperture 22 may be formed at first and second angular positions, respectively, in the enclosure 12. For example, as shown in FIGS. 3 and 4, the first aperture 20 may be positioned about 180 degrees apart from the second aperture 22 about the enclosure 12. Notably, the apertures 20, 22 are formed in the body or enclosure 12, which, as described above, may be of a single or continuous or fixed design, such that no moving or adjustable parts are necessary or implicated in forming the apertures 20, 22. This provides a robust design that, as will be described, is advantageous to ensuring proper placement and operation of the retractor 10 during a minimally invasive procedure. That is, adjustable or retractable or non-fixed retractor designs can inject undesired complexity that can negatively affect the ability to perform the procedures that will be described herein in a minimally-invasive manner.

The first aperture 20 may oppose the second aperture 22 to form a passage extending transverse to the axis, A, from the first aperture 20, through the lumen 18, and to the second aperture 22. The dimensions of the first aperture 20 and second aperture 22 may be sized to accommodate one or more components included in the present systems and methods. For example, the first aperture 20 and the second aperture 22 may be sized receive a trocar for delivering a graft material to the spine. Accordingly, two or more retractors 10 may be arranged to provide a passage along the spine of a patient as will be described herein.

Figure 5:
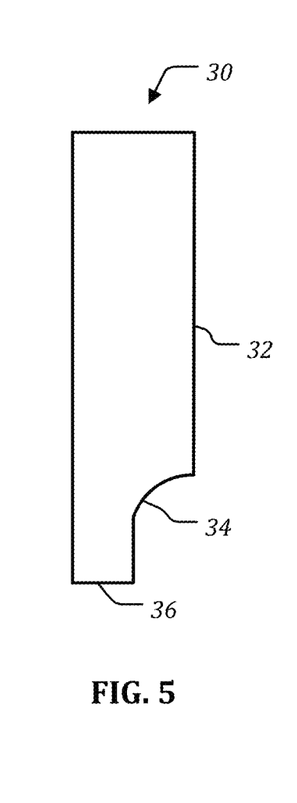
FIG. 5 is a front elevational view of another retractor according to the present disclosure.
Figure 6:
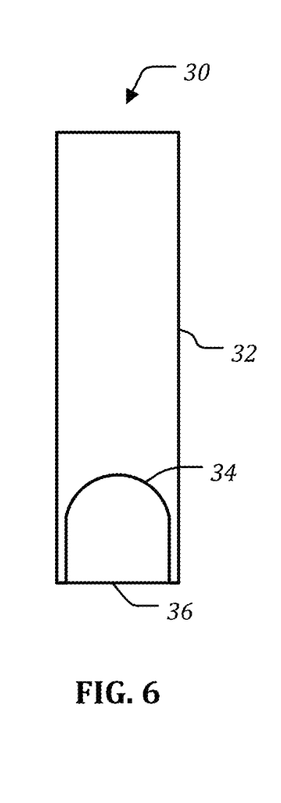
FIG. 6 is a side elevational view of the retractor of FIG. 5.
Figure 7:
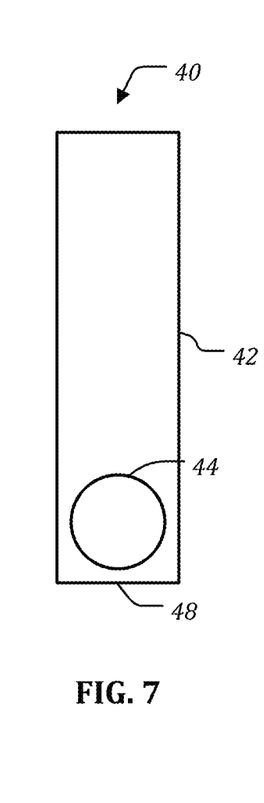
FIG. 7 is a front elevational view of a yet another retractor according to the present disclosure.
Figure 8:
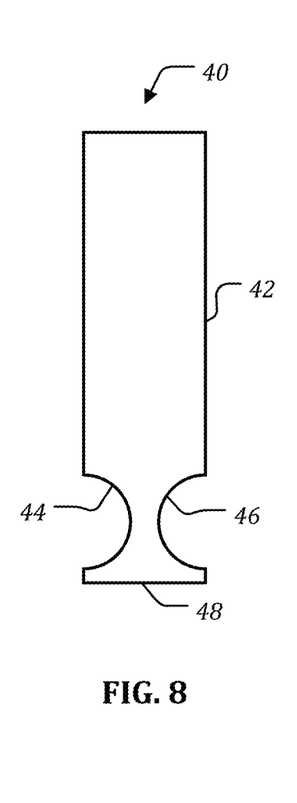
FIG. 8 is a side elevational view of the retractor of FIG. 7.

While, the first aperture 20 and the second aperture 22 may be U-shaped or semi-circular shaped as shown in FIGS. 1-4, other aperture configurations may be possible. For example, FIGS. 5-8 show two different variations of retractor 12. In one example, FIGS. 5 and 6 show a retractor 30 defining an enclosure 32 with a single aperture 34 extending in a longitudinal direction along the length of the enclosure 32 from a first end 36. Aperture 34 may generally correspond with first aperture 20 in that it a generally U-shaped or semi-circular shaped arch. By comparison, FIGS. 7 and 8 shown a retractor 40 defining an enclosure 42 with a first aperture 44 and a second aperture 46 positioned proximate a first end 48 of the enclosure 42. The first aperture 44 and the second aperture 46 do not intersect with or extend from the first end 48. Instead, the first aperture 44 and the second aperture 46 are positioned at an intermediate positioned in the enclosure 42. Notably, both aperture 34 in retractor 30 and first aperture 44 and second aperture 46 in retractor 40 define a passage sized to accommodate one or more components such as a trocar according to the present disclosure.

In one aspect, the retractors may be used during spinal fusion surgery in conjunction with a series of dilators to expand an incision within the body of a patient. For example, a dilator may be placed into incision proximate a target area over the transverse process of a vertebra. The incision may be enlarged by gradually adding larger dilators. Once the desired incision size has been made, a retractor may be placed on the outside of the dilators and the dilators within may be removed. The retractors may then hold back the tissue during a surgical procedure. In some embodiments, a retractor may serve multiple purposes. For example, a retractor may be used to hold open an incision for a surgeon to decorticate the surface of the affected vertebrae or ensure proper insertion of stability hardware such as pedicle screws. The retractor may include an aperture such as an arch formed at a proximal end of the retractor to allow a trocar to pass through the apertures on adjacent retractors positioned along the spine. The retractor may provide a visual window through the opening in the incision to enable a user such as a surgeon to view the transverse processes such as for confirmation of proper graft placement.

A retractor according to the present disclosure can be fabricated from any suitable material. In one example, a retractor may be fabricated from polyether ether ketone (PEEK), which is a thermoplastic material that is generally compatibility with surgical procedures. Other materials may include polymers, polymer composites, metals, ceramics, glass, stainless steel, cobalt base alloys, bioceramics, titanium alloys, and pure titanium. Moreover, the retractor may be fabricated from a radiolucent or radio-opaque material. For example, a radiolucent retractor may be provided to facilitate imaging of the patient during a surgical procedure.

Figure 9:
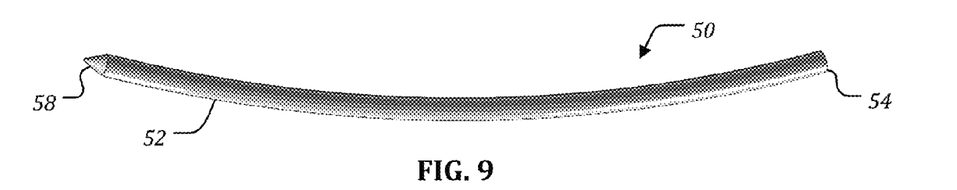
FIG. 9 is a perspective view of an example trocar according to the present disclosure.
Figure 10:
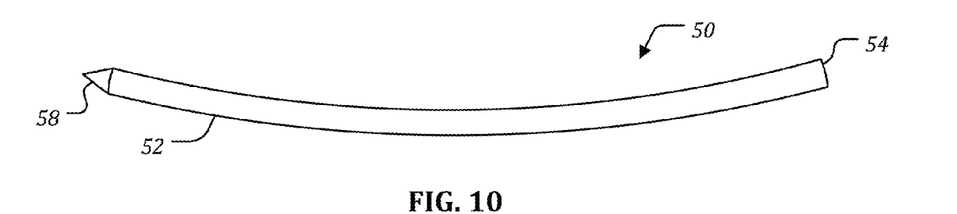
FIG. 10 is a front elevational view of trocar of FIG. 9.
Figure 11:
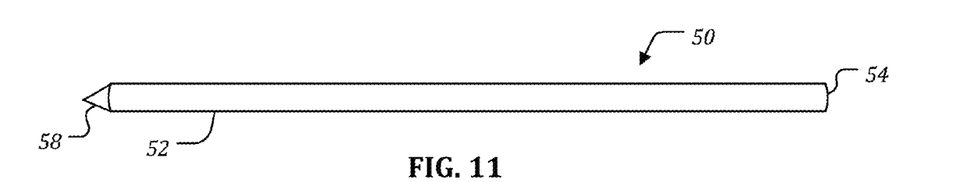
FIG. 11 is a top plan view of the trocar of FIGS. 9 and 10.
Figure 12:
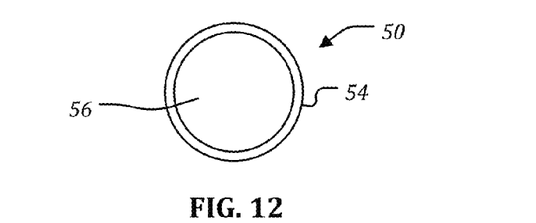
FIG. 12 is a side elevational view showing an open end of the trocar of FIG. 9.

A system and method according to the present disclosure may further include a trocar or other like passing or implantation device. The trocar can have any suitable design, such as a single incision sheath design, a double incision sheath design. Furthermore, the trocar can be designed to support a graft material either internally or externally. One example of a trocar 50 having a double incision sheath design is shown in FIGS. 9-11. Trocar 50 can include an elongate rod 52 having a first open end 54 and defining an interior space 56 for receiving a graft material (not shown). The trocar may additionally (or alternatively) include a second end 58 having a closed, conical or tapered construction for cutting or navigating through tissue to facilitate guidance of a graft material into place within a patient.

In one aspect, the elongate rod 52 may have a rigid construction, for example, to support a graft material or to facilitate passage of the trocar 50 through the various tissues of the patient. In another aspect, the elongate rod 52 may be curved from to center to allow for passage of the trocar 50 in a single, smooth motion. The angle of the trocar may be varied depending the factors such as the dimensions of the patient (height, weight, girth) the dimensions of the patients spine and the number of the vertebrae to be treated, and the dimensions of the graft material. In one example, a trocar may have an angle of curvature of between about 5 degrees and about 25 degrees, or less than 35 degrees and, generally, less than 90 degrees. In another aspect, the trocar may have an angle of curvature of about 30 degrees. In one aspect, a trocar with a smaller angle of curvature may increase the amount of contact between the implantation device and the spine, thereby increasing the number of targeted vertebrae the trocar can contact and deliver graft material to. In another aspect, a trocar with a larger angle of curvature may be able to run a bone graft along a longer path, therefore allowing the fusion of more vertebrae.

In one aspect, the double incision sheath design of trocar 50 may not require any mechanical manipulations or moving parts. The lack of mechanical parts may enable a more straightforward operation of the trocar. Moreover, the closed-tipped design of the trocar 50 may reduce catching or tearing of the surrounding tissue on the trocar 50.

As in the case of the retractor 10, the trocar 50 may be formed from any suitable material including polymers, polymer composites, metals, ceramics, glass, stainless steel, cobalt base alloys, bioceramics, titanium alloys, and pure titanium. Moreover, the retractor may be fabricated from a radiolucent or radio-opaque material as discussed previously. In one example, the trocar may be formed from medical grade stainless steel. In one aspect, the trocar 50 may be reusable as stainless steel may be sterilized in an autoclave. Stainless steel may also be a cost-effective material for the manufacture of the trocar. In another example, the trocar 50 may be fabricated from a malleable material, allowing the user (e.g., surgeon) to bend it to a patient-specific curvature. In one aspect, a biocompatible material such as aluminum may be used to provide rigidity, while still allowing slight deformation with the user's effort. In some embodiments, a small hole may be added in the side of the second end 58 to facilitate cleaning of the trocar 50.

While one embodiment of a trocar is shown with a double incision sheath design, other trocar designs may be compatible with the present system and method. For example, a trocar may have a single incision sheath design. The single incision sheath design trocar may have a design similar to that of trocar 50. In one aspect, trocar 50 may be modified to have a single incision sheath design by converting second end 58 to be mechanically operable to open once the trocar has been properly positioned within the patient. Accordingly, operation of a single incision sheath can include a first step of inserting a tapered end of the trocar into a primary incision. The trocar may then be guided or passed along the decorticated region of the spine where the bone graft material is to be implanted. Once the trocar has been positioned adjacent the target vertebrae, the tapered second end of the trocar may be mechanically opened to enable the graft material to exit the trocar from the second end and be deposited along the decorticated spine as the device is retracted in the reverse direction through the primary incision.

In one aspect, a small opening in the tip of the tapered end may be included in the design of the single incision sheath type trocar to enable a biodegradable suture to protrude out of the end. This suture may be used to ensure that the bone graft remains in place as the sheath is removed via the primary incision. Placement of the graft material may be achieved by securing the suture with a clamp that has been designed to fit into the retractor. Upon securing the furthest end of the bone graft, the sheath may be pulled backwards while the bone graft remains securely in place.

Figure 13:
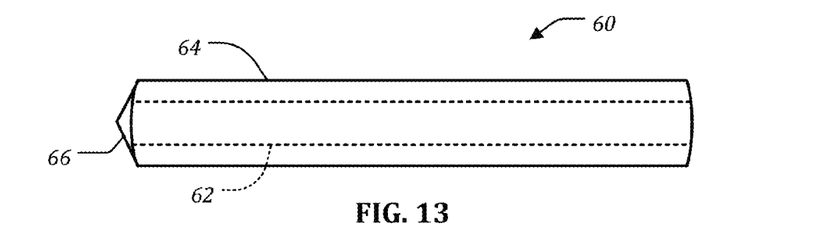
FIG. 13 is a top plan view another trocar for supporting a tubular graft about an exterior of the trocar according to the present disclosure.

In yet another embodiment, a trocar can include a design for supporting a tubular graft about an exterior of the trocar. With reference to FIG. 13, a trocar 60 having an exterior graft design may include an elongate rod 62 surrounded by a tubular shaped graft material 64. An end 66 of the rod 62 may include a conical or tapered cap for cutting or passing through tissue to guide the graft material 66 into place within a patient. The end 66 may protect the graft material 64, which may include a casing, from damage (e.g., tearing) during insertion by forming a path in the tissue for the graft material 64 to pass through. As in the case of other embodiments of trocars described herein, trocar 60 may have an angle of curvature to allow for insertion of the graft material 64 in a single, smooth application. The angle of the trocar 60 may be varied depending factors such as the dimensions of the patient (height, weights, girth) the dimensions of the patients spine and the number of the vertebrae to be treated, and the dimensions of the graft material. In one example, a trocar 60 may have an angle of curvature of between about 5 degrees and about 25 degrees, or less than 35 degrees and, generally, less than 90 degrees. In another example, the trocar 60 may have an angle of curvature of about 30 degrees.

In one aspect, the rigidity or flexibility of a trocar according to the present disclosure may be tailored to the properties of the graft material. For example, a graft material provided in a flexible bag or mesh may require a more rigid passing device to add stiffness as the graft material is guided past body tissues.

In another aspect, for a trocar that may be guided by hand, the ergonomics of the trocar may be modified. Bodily fluids such as blood may end up coating the device upon implantation, which may reduce the surgeon's ability to grip the trocar. In order to improve the user's grip, embodiments of a trocar may be provided with indentations for hand placement or a biocompatible grip material. In the case of a double incision sheath design for a trocar, it may be useful to enable a handle or other grip modification to travel through the pathway of the insertion or be removable from the trocar.

Figure 14:
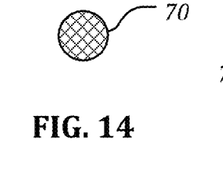
FIG. 14 is a schematic illustration of an embodiment of a graft material.

In some embodiments, a system and method can include a graft material. With reference to FIG. 14, a graft material 70 may be provided to facilitate fusion of adjacent vertebrae. Bone graft may be autografted from the patient such as from a patient's pelvic bone. Additionally or alternatively, the bone graft may be obtained as an allograft from a cadaver or other donor. The graft material may be provided in any suitable format, such as in the form of a powder, chips, grounds, a paste, a putty and the like. In one aspect, the graft material may be provided as a stand-alone material.

Figure 15:
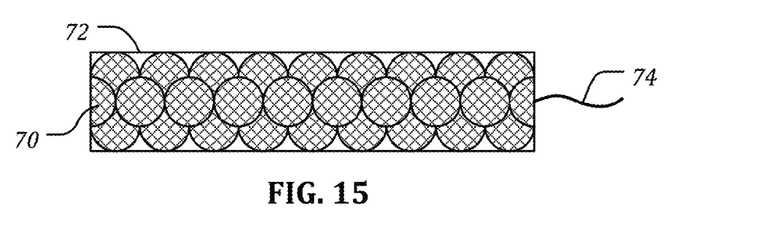
FIG. 15 is a schematic illustration of a housing filled with the graft material of FIG. 14.
Figure 16:
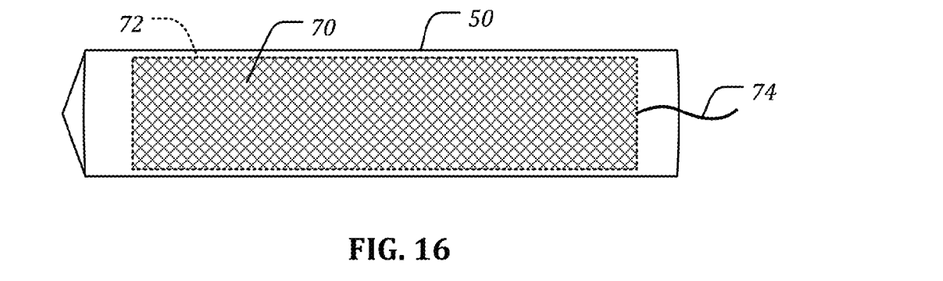
FIG. 16 is a schematic illustration of the graft material and housing of the FIG. 15 positioned within the trocar of FIG. 9.

Turning to FIGS. 15 and 16, a trocar according to the present disclosure may be used to deliver the graft material 70 along the spine of a patient. However, depending on the design of the trocar, it may be useful to deliver the graft material 70 within a biocompatible encasement material or housing 72 for placement and localization of the graft material 70 in the body of the patient. In some embodiments, the graft material 70 may be partially or fully enclosed within the housing 72 or other form of encasement. Examples of housings 72 that may be used can include a rigid metal cage, an absorbable collagen sponge soaked with a solution containing recombinant human bone morphogenetic protein-2, a titanium mesh cage, gauze or a mesh such as a polymer mesh. In one aspect, the use of a mesh or cage can enable osteoblasts to move from the graft material 70 to the decorticated vertebrae and facilitate fusion. In some embodiments, the housing 72 may be rigid or flexible. For example, a rigid cage may allow for the graft to more easily be guided percutaneously. In another example, a more flexible material may be more readily loaded into a trocar (e.g., trocar 50), or shaped/positioned once instead the patient.

In one aspect, a graft material 70 housing can include a polymer or copolymer housing 72. For example, polylactic acid (PLA) and polyglycolic acid (PGA) are biodegradable, non-toxic polymers that may be used to form a housing for a graft material 70. PLA and PGA may be combined to form a poly lactic-co-glycolic acid copolymer (PLA-co-PGA), with properties controlled by the ratio of PLA to PGA. In one aspect PLA-co-PGA polymers may be permeable to cells such as osteoblasts. Furthermore, adding pores or utilizing a mesh structure may increase osteoconductivity. If a more rigid encasement is desired, a PLA-co-PGA copolymer with a higher ratio of PGA can be used, while a higher ratio of PLA may be used to create a flexible bag-like housing 72. The appropriate PLA-co-PGA ratio may be determined to achieve the correct osteoconductivity, encasement strength, and degradation rates. Other methods of providing a graft material 70 such as a mesh encasement fabricated from polyethylene terephthalate (PET) may also be used.

In some embodiments, the material selected for the housing 72 may be supplied in sheets of varying sizes, which may be wrapped around the graft material 70 (e.g., bone chips) and secured, for example, with a synthetic absorbable suture. One suitable suture may include polyglycolic acid (e.g., a vicryl suture). Complete absorption of the suture material may occur within about thirty to about ninety days, which may be after the initiation of the bone fusion process. In some embodiments, the material selected for the housing 72 may be impregnated with an antibacterial agent such as tricolsan to provide antimicrobial protection.

In some embodiments, a biodegradable string 74 may be provided at the end of the graft material 70 or housing 72 to allow the graft material 70 to be removed from the trocar (e.g., trocar 50). When the end of the trocar is at the target graft location, the user may grasp the string 74 and remove the trocar from the second incision, thus releasing the graft material 70. In one aspect, the string 74 may be made of the same material as the graft encasement so that degradation occurs at the same rate. For example, an absorbable suture may be configured for this use.

Figure 17:
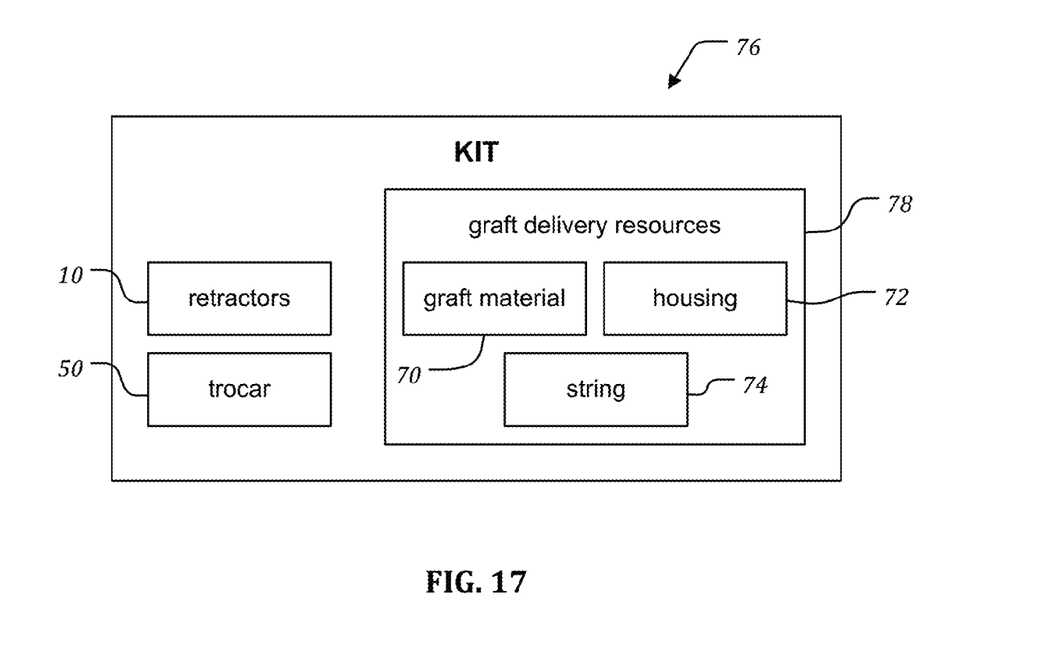
FIG. 17 is a schematic illustration of an embodiment of a kit including at least one retractor, a trocar and one or more graft material resources, such as a graft material, a housing or a biodegradable string.

In some embodiments, a kit may be provided for delivering graft material to the spine of a patient. As shown in FIG. 17, one embodiment of a kit 76 may include one or more of the components described herein, such as one or more retractors, trocars graft materials, or other like components. For example, the kit 76 may include at least one retractor 10 for insertion in an incision proximal to a spine of a patient, and at least one trocar 50 for delivering a graft material 70 to the spine of the patient in combination with the at least one retractor 10. Optionally, the kit 76 may include one or more graft delivery resources 78, such as the graft material 70, the housing 72 the string 74, or other like components. In general, one or more components may be added, substituted or omitted in providing a kit, such as the kit 76. Particularly, the graft material 70 may not be included in the kit 76 and, in some configurations, the graft delivery resources 78 may be omitted from the kit 76 and otherwise sourced.

Figure 18:
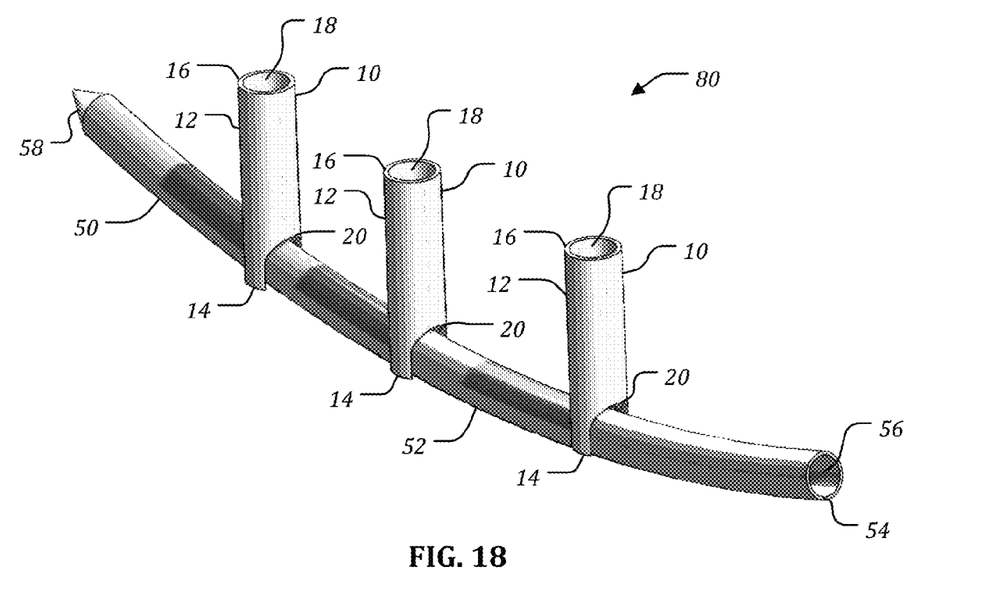
FIG. 18 is perspective view showing an assembly including a trocar guided through a passage formed by a set of retractors in accordance with the present disclosure.
Figure 19:
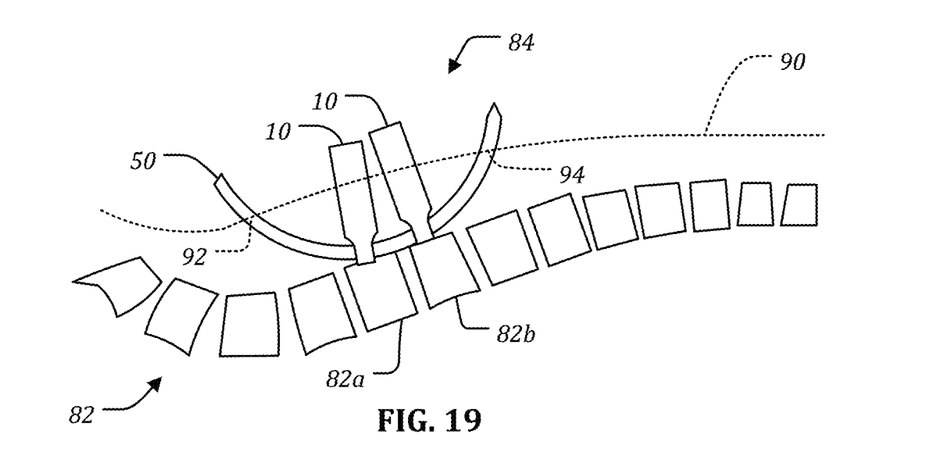
FIG. 19 is a side elevational view showing another configuration of the assembly of FIG. 18 positioned along the spine of a patient.
Figure 20:
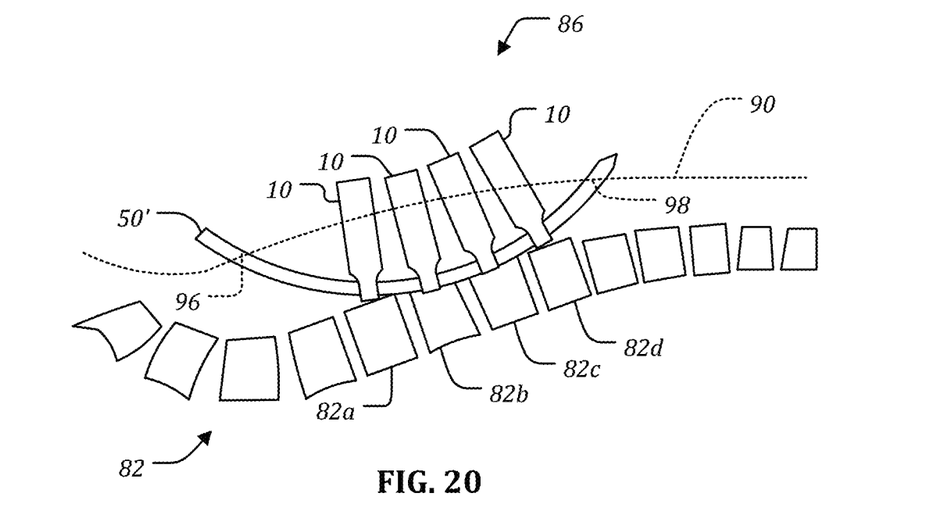
FIG. 20 is a side elevational view showing yet another configuration of the assembly of FIG. 18 positioned along the spine of a patient.

In operation, a system and method according to the present disclosure may include delivering a graft material to a spine of a patient. With reference to FIG. 18, one example of an assembly 80 may include a set of three retractors 10 and a trocar 50 having a double incision sheath design. While FIGS. 18-20 show one type of retractor and trocar, other embodiments of retractors or trocars may be used to implement the present system and method. One example may include a different retractors design such as retractor 30, or a combination of retractor designs.

As shown in FIG. 18, a trocar 50 may function as a rigid guide for positioning a graft material (not shown) adjacent one or more decorticated vertebrae. The graft material may be inserted into the interior space 56. Thereafter, the second end 58 of the elongate rod 52 may be passed into the patient through a primary incision. Once properly inserted along the spine, the trocar 50 may be guided along the decorticated region of the vertebrae. The curvature of the trocar 50 may allow for the device to be pushed back out of a secondary incision spaced apart from the first incision within the patient. In one aspect, the trocar 50 may be guided from the primary incision to the secondary incision in one single, continuous motion.

The graft encasement located at the end of the trocar may be directed along the decorticated region until the back end of the device reached the vertebrae requiring fusion. At this point, the user may secure a suture attached to the inferior end of the bone graft encasement. This may ensure that the encased bone graft would be secured in place while the trocar continues to move in a forward direction towards a second incision, which may be parallel to the first incision. The presence of this second incision may simplify the procedure. In another aspect, the second incision may allow for the user to more quickly or accurately place the bone graft along the injured vertebrae. The second incision may further allow for easier device extraction.

With continued reference to FIG. 18, the retractors 10 may be aligned such that apertures 20 and apertures 22 form a passage through which trocar 50 may be guided. Accordingly, apertures 20 and apertures 22 may accommodate the dimensions of the elongate rod 52 of the trocar 50 with the longitudinal axis of retractors 10 extending orthogonally from a longitudinal axis of the trocar 50.

Turning to FIGS. 19-20, it may be seen that the angle of curvature of a trocar may be selected based on the number of vertebrae to be treated. In one aspect, a section of a spine 82 may include one or more vertebrae such vertebra 82a, vertebra 82b, vertebra 82c and vertebra 82d. The spine 82 of a patient is positioned beneath layers of tissue having an exterior (anterior) surface 90. Initially, retractors 10 may be positioned relative to the target vertebrae through respective incisions formed in the surface 90. For example, in FIG. 19, an assembly 84 includes two retractors 10 positioned relative to corresponding target vertebrae 82a and 82b, whereas in FIG. 20, an assembly 86 includes four retractors 10 positioned relative to corresponding target vertebrae 82a, 82b, 82c and 82d.

In FIG. 19, a trocar 50 having a first angle of curvature configured to treat target vertebrae 82a and 82b may be inserted through a primary incision 92 in exterior surface 90. The trocar 50 may then be guided through the passage formed in part by retractors 10 and out of exterior surface 90 through a secondary incision 94. The angle of curvature of trocar 50 may enable a user to guide the trocar 50 into and out of the patient through exterior surface 90 while positioning a graft material enclosed within the trocar 50 at a position for treating target vertebrae 82a and 82b.

By comparison, FIG. 20 shows a second assembly 86 including a trocar 50' having a second (larger) angle of curvature configured to treat target vertebrae 82a, 82b, 82c and 82d. Trocar 50' may be inserted through a primary incision 96 in exterior surface 90. The trocar 50' may then be guided through the passage formed in part by retractors 10 and out of exterior surface 90 through a secondary incision 98. The larger angle of curvature of trocar 50' enables a user to guide the trocar 50' into and out of the patient through exterior surface 90 while positioning a graft material enclosed within the trocar 50' at a position for treating target vertebrae 82a, 82b, 82c and 82d.

Figure 21A:
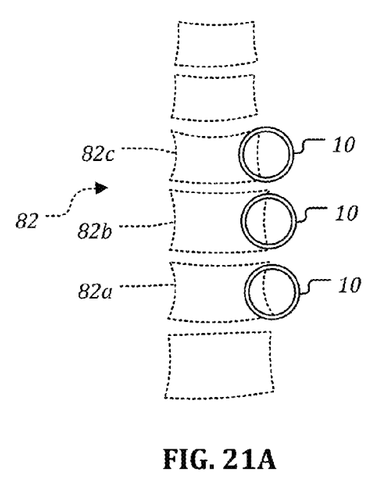
FIG. 21A shows a set of retractors positioned relative to the spine of a patient.
Figure 21B:
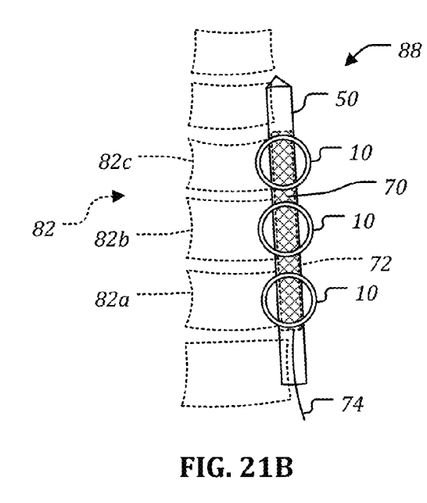
FIG. 21B shows a trocar housing a graft material. The trocar was guided through the retractors in order to position the trocar along the spine of the patient.
Figure 21C:
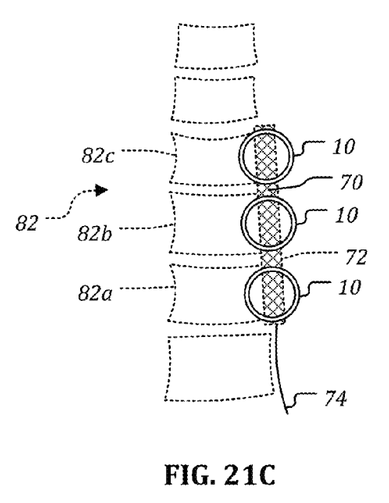
FIG. 21C shows the graft material positioned along the spine of the patient after removal of the trocar.

With reference to FIGS. 21A-21D, in some embodiments, while the user is guiding a trocar such as trocar 50 through one or more retractors 10, the positioning of the trocar 50 may be observed within the interior space defined by the retractors 10 as illustrated for an assembly 88 in FIG. 21B. Accordingly, a user, such as a surgeon, may be provided with both visual and tactile feedback during an operation including one or more components of the assembly 88. In particular, a user may first position retractors 10 relative to target vertebrae 82a, 82b and 82c as shown in FIG. 21A. Thereafter, the user may guide the trocar 50 through a primary incision, through the retractors 10 and through a secondary incision as shown in FIG. 21B. In one aspect, the trocar may be loaded with a graft material 70 within a housing 72. In another aspect, the user may confirm the position of the trocar 50 by viewing portions of the trocar 50 through the interior of the retractors 10. The user may then secure the string 74 coupled to the graft material 70 or housing 72 while removing the trocar 50. In one aspect, this may result in alignment of the graft material 70 relative to the target vertebrae 82a, 82b and 82c as shown in FIG. 21C.

Figure 21D:
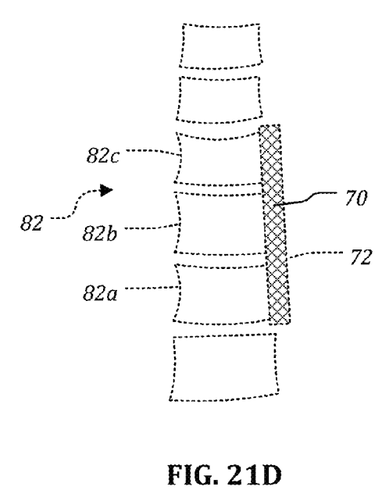
FIG. 21D shows a view of FIG. 21C after removal of the retractors.

The user may then remove the retractors 10 and optionally the string 74 from the patient as shown in FIG. 21D.

Figure 22:
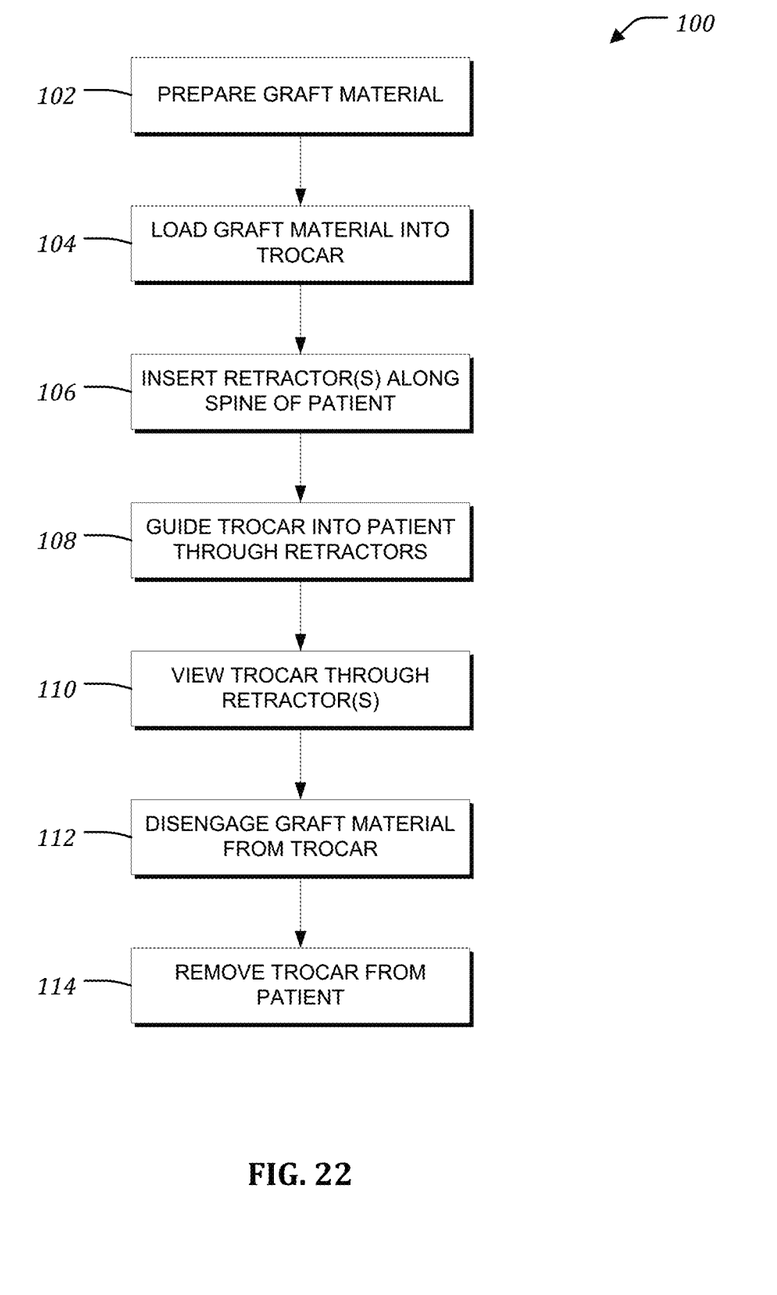
FIG. 22 is flow chart setting forth some examples steps in an example method for delivering a graft material to a spine of a patient.

Turning to FIG. 22, an example method 100 for delivering a graft material to a spine of a patient can include a step 102 in which a graft material such as a bone graft material is prepared for insertion within a patient. Step 102 may include harvesting, processing, acquiring, encasing or otherwise treating a graft material to prepare the graft material for use in a later step of the method 100. In a next step 104, the graft material may be loaded into a trocar. In one example, morselized bone may be loaded directly into an open end of a trocar. In another example, a graft material may be encased in a mesh or other housing. The encased graft material may then be loaded into the trocar.

A next step 106 of the method 100 may include inserting at least one retractor along the spine of the patient. As described above, the retractor may form an enclosure extending between a first open end and a second open end and having a passage located proximate to the first open end that extends through the enclosure to arrange the passage along the spine of the patient. In one aspect, the passage may extend in a longitudinal direction transverse to a lumen formed between the first open end and the second open end of the enclosure. Example retractors may include retractor 10, retractor 30 or retractor 40. A further step 108 may include guiding the trocar into the patient through the apertures formed in the one or more retractors. In one aspect, the trocar may include the graft material loaded into an interior space as described in step 102 and step 104 of the method 100.

A next step 110 of the method 100 may include viewing the trocar through at least one retractor. The trocar may be viewed, for example, to arrange the trocar along the spine of the patient. Thereafter, in a step 112, the graft material may be disengaged from the trocar. A step 114 may then include removing the trocar from the patient. In one example, the trocar may be guided through the passage of the at least one retractor while the graft material is held in place within the patient, thereby delivering the graft material to the spine of the patient. With respect to a double incision sheath design trocar (e.g., trocar 50), step 114 may include guiding the trocar through the at least one retractor in a first direction and removing the trocar from the passage of the at least one retractor in the first direction.

EXAMPLES

A prototype device for minimally invasive delivery of a graft material to the decorticated spine of a patient for developed and tested with a model spine section. A trocar was formed from a hollow tube made of stainless steel. The use of a hollow trocar provided a containment area for the graft material during insertion along the decorticated vertebrae. The trocar measured 382 mm in length and included an angle of curvature from the center of about 30 degrees. The angle of curvature contributed to the insertion and removal of the device in a smooth and linear fashion. The width of the trocar was 13 mm with a wall thickness of 1 mm. The overall length of the trocar was selected based on a distance between vertebral centers of 37 mm for an average adult patient as well as the criteria that the device be able to deliver a graft material to up to 6 vertebrae. An additional 160 mm were added to the length of the trocar. In one aspect, the curvature of the trocar may ensure that only a small portion of the trocar comes into contact with the vertebrae at one time.

A series of prototype retractors were prepared with a 3D printer. Each retractor included an enclosure extending from a first open end to a second open end to form a lumen extending along an axis therebetween and that is accessible from the first open end and the second open end. The enclosure had an outer diameter of 1.8 cm, a thickness of 0.15 cm and a length of 7 cm. The length of the retractor was based on a muscle thickness on the anterior of the spine of 5 cm for an average adult. The length of the retractor was increased by additional 2 cm to enable to the retractor to protrude from the patient's back once inserted.

The retractors further included a first aperture formed at first angular position in the enclosure and a second aperture formed at second angular position in the enclosure and opposing the first aperture to form a passage extending transverse to the axis from the first aperture, through the lumen, and to the second aperture. The first and second apertures were located proximate to the first open end and included semi-circular or U-shaped arches with a height of 1.5 cm and a radius of curvature of 1.5 cm. The dimensions of the apertures were selected to accommodate the 1.4 cm diameter of the trocar. Accordingly, the retractors may be positioned with the first aperture and second aperture sized to arrange the passage along a spine of a patient to receive the trocar for delivering a graft material to the spine.

A model bone graft was prepared for insertion into the trocar. The graft material had a length of 10 cm and a diameter of 1 cm. The model bone graft included a crushed inert material selected approximate a commercially available bone allograft material. The materials were encased in loosely woven mesh gauze. The gauze was secured around the graft with a thin string selected to approximate a biocompatible suture material. An anchor string was fastened to the gauze and extended for about 40 to about 50 cm from one end of the graft material. The anchor string was included to enable a user to hold the graft material in place during extraction of the trocar.

A model spine section was prepared by encasing an anatomically accurate spine model three vertebrae in length within a volume of KNOX gelatin. The gelatin was prepared as a 10 wt % aqueous solution of KNOX gelatin to approximate the resistance of a patient's tissue. The spine section contained relevant anatomical components, including transverse processes, vertebral bodies and spinal disks. The spine section model was 8.25 cm in length and 7.5 cm wide, with the widest point being at the transverse processes. The model spine section was placed in a rectangular container with the transverse processes facing up. The container had a length and width sized to accommodate the dimensions of the model spin section. The KNOX solution was poured until the tops of the transverse processes were covered by approximately 2 cm.

The bone graft material was pushed into the open end of the hollow trocar with the string trailing out the distal end of the trocar until the graft material was no longer visible. The retractors were pushed down over the transverse processes and the gelatin material within the retractors was removed. The retractors were set in place over the transverse processes. The retractors provided visual confirmation of the location of the model spine section by viewing through the open ends of the retractors. The retractors were rotated until the apertures were visually aligned with the along the model spine section.

The trocar was inserted slightly above the submerged spine and directed through the first retractor opening. Upon reaching the opening, the edges of the retractor provided tactile feedback to the user as to whether or not the trocar was successfully guided through the opening. The user was able to view the spine through the retractors to observe the whether the trocar had passed through the retractor. The trocar was continuously pushed through a fist retractor and then through a second and third adjacent retractor. The trocar was continuously passed along the length of the model spine and the natural curvature of the trocar led to the exit of the trocar from the gelatin at a second location. As the trocar emerged from the gelatin, the user was able to grasp the first end of the trocar that had initially been inserted into the gel in order to pull the trocar into position relative to the model spine section. With the trocar positioned at the desired location, the anchor string extending from the second end of the trocar was grasped and held by the user. Holding onto the anchor string prevented the continued movement of the bone graft with the trocar. The trocar was continuously removed from the gelatin and the bone graft remained in place right along the transverse processes. The trocar was completely removed from the gelatin along with the retractors while the bone graft remained in the target location. The anchor suture used to secure the device was then removed.

In general, the experimental procedure with the prototype components demonstrated successful placement of the model bone graft along the transverse processes. Bone graft was successfully placed within 2 mm of the transverse processes. In one aspect, accurate placement of the graft material was enabled by the design of the retractors, which provided both visual and tactile feedback to the user. In particular, the retractors provided tactile feedback to the user while guiding the trocar through the apertures with visual feedback provided though the openings in the first and second ends of the The schematic flow charts shown in the Figures are generally set forth as a logical flow chart diagram. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed in the Figures are provided to explain the logical steps of the method and are understood not to limit the scope of the method. Although various arrow types and line types may be employed, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present disclosure has been described in terms of one or more preferred embodiments, and it should be appreciated that many equivalents, alternatives, variations, and modifications, aside from those expressly stated, are possible and within the scope of the invention.

While present inventive concepts have been described with reference to particular embodiments, those of ordinary skill in the art will appreciate that various substitutions and/or other alterations may be made to the embodiments without departing from the spirit of present inventive concepts. Accordingly, the foregoing description is meant to be exemplary, and does not limit the scope of present inventive concepts.

A number of examples have been described herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

The invention claimed is:

1. A kit for delivering graft material to a spine of a patient, comprising:
   at least one retractor for insertion in an incision proximal to a spine of a patient, the retractor including:
      an enclosure extending from a first open end to a second open end to form a lumen extending along an axis therebetween;
      a first aperture formed in the enclosure at a first angular position in the enclosure; and
      a second aperture formed in the enclosure at a second angular position in the enclosure and opposing the first aperture to form a passage from the first aperture, through the lumen, and to the second aperture; and
   a trocar for delivering a graft material to the spine of the patient, the trocar including an elongated rod having a first open end and defining an interior space for receiving the graft material, the interior space extending along a longitudinal axis defined by the elongated rod,
   wherein the first and second apertures are dimensioned to receive the elongated rod of the trocar such that the elongated rod extends through the passage and the longitudinal axis defined by the elongated rod is arranged transverse to the axis defined by the enclosure to arrange the graft material along the spine of the patient.

2. The device of claim 1, wherein the first aperture and the second aperture extend in a longitudinal direction transverse to the axis extending along the enclosure from the first open end to the second open end.

3. The device claim 2, wherein the first aperture and the second aperture are one of U-shaped and semi-circular shaped.

4. The device of claim 1, wherein the first open end of the retractor is sized to be receivable within the incision in the patient to be arranged proximate to the spine.

5. The device of claim 1, wherein the first angular position is 180 degrees from the second angular position.

6. The device of claim 1, wherein the enclosure defines a generally cylindrical body.

7. The device of claim 1, wherein the trocar has an angle of curvature.

8. A system for delivering graft material to a spine of a patient, comprising:
   at least one retractor for insertion in an incision proximal to a spine of a patient, the retractor including:
      an enclosure extending from a first open end to a second open end to form a lumen extending along an axis therebetween;
      a first aperture formed in the enclosure at a first angular position in the enclosure; and
      a second aperture formed in the enclosure at a second angular position in the enclosure and opposing the first aperture to form a passage from the first aperture, through the lumen, and to the second aperture; and
   a trocar for delivering a graft material to the spine of the patient, the trocar including an elongated rod having a first open end and defining an interior space for receiving the graft material, the interior space extending along a longitudinal axis defined by the elongated rod,
   wherein the first and second apertures are dimensioned to receive the elongated rod of the trocar such that the elongated rod extends through the passage and the longitudinal axis defined by the elongated rod is arranged transverse to the axis defined by the enclosure to arrange the graft material along the spine of the patient.

9. The system of claim 8, wherein the first aperture and the second aperture extend in a longitudinal direction transverse to the axis extending along the enclosure from the first open end to the second open end.

10. The system claim 9, wherein the first aperture and the second aperture are one of U-shaped and semi-circular shaped.

11. The system of claim 8, wherein the first open end of the retractor is sized to be receivable within the incision in the patient to be arranged proximate to the spine.

12. The system of claim 8, wherein the first angular position is 180 degrees from the second angular position.

13. The system of claim 8, wherein the enclosure defines a generally cylindrical body.

14. The system of claim 8, wherein the trocar has an angle of curvature.

* * * * *